United States Patent [19]

Debras et al.

[11] Patent Number: 4,613,724

[45] Date of Patent: Sep. 23, 1986

[54] PROCESS FOR REMOVING CARBONYL-SULFIDE FROM LIQUID HYDROCARBON FEEDSTOCKS

[75] Inventors: Guy L. G. Debras, Belgrade; Georges E. M. J. De Clippeleir, Sint-Pieters-Leeun; Raymond M. Cahen, Brussels, all of Belgium

[73] Assignee: Labofina, S.A., Brussels, Belgium

[21] Appl. No.: 753,288

[22] Filed: Jul. 9, 1985

[51] Int. Cl.$^4$ .................... C07C 7/00; C07C 11/00
[52] U.S. Cl. .................... 585/824; 208/244; 423/244; 585/855
[58] Field of Search ............ 208/208 R, 244, 247, 208/310 R; 585/820, 824, 850, 855; 423/244 R

[56] References Cited

U.S. PATENT DOCUMENTS

| | | | |
|---|---|---|---|
| 2,772,208 | 11/1956 | Ferm | 585/824 X |
| 2,951,034 | 8/1960 | Stuart | 585/850 X |
| 2,959,538 | 11/1960 | Weikart et al. | 208/244 X |
| 3,058,800 | 10/1962 | Frevel et al. | 585/824 X |
| 3,864,412 | 2/1975 | Murphy | 585/824 |
| 3,998,902 | 12/1976 | Foster et al. | 585/850 X |
| 4,083,887 | 4/1978 | Foster et al. | 585/855 X |
| 4,150,063 | 4/1979 | Besozzi et al. | 585/855 X |
| 4,533,529 | 8/1985 | Lee | 423/244 X |

FOREIGN PATENT DOCUMENTS

| | | | |
|---|---|---|---|
| 809584 | 4/1969 | Canada | 423/244 R |
| 2304963 | 2/1972 | Fed. Rep. of Germany | 585/855 |
| 1142339 | 2/1969 | United Kingdom | 208/244 |
| 596273 | 3/1978 | U.S.S.R. | 423/244 R |

*Primary Examiner*—Andrew H. Metz
*Assistant Examiner*—Glenn A. Caldarola
*Attorney, Agent, or Firm*—John K. Abokhair; M. Norwood Cheairs

[57] ABSTRACT

The present invention relates to a process for removing carbonyl sulfide from a liquid olefinic hydrocarbon feedstock comprising (a) passing said hydrocarbon feedstock over an absorbent material comprising zinc oxide and a promoter selected from the group consisting of alumina, silico-aluminas and any combination thereof; and (b) recovering a liquid olefinic hydrocarbon stream having a substantially reduced carbonyl sulfide content.

20 Claims, No Drawings

PROCESS FOR REMOVING CARBONYL-SULFIDE FROM LIQUID HYDROCARBON FEEDSTOCKS

FIELD OF THE INVENTION

The present invention relates to a process for removing sulfur, present in the form of carbon oxysulfide or carbonyl sulfide, from liquid hydrocarbons. More particularly, the present invention relates to a process for the removal of carbonyl sulfide from hydrocarbon feedstocks containing propylene.

BACKGROUND OF THE INVENTION

Industrial applications of liquid hydrocarbons and particularly, liquified olefinic hydrocarbons, has become more increasingly specialized. The technology as presently developed utilizes highly efficient catalysts to convert these liquified hydrocarbon feedstocks into final product such as polymers. However, these highly efficient catalysts are very sensitive to contaminants, particularly sulfur contaminants, found in these hydrocarbon feedstocks.

In addition to the well known sulfur compounds such as hydrogen sulfide and mercaptans, the hydrocarbon feedstocks normally contain a small quantity of carbonyl sulfide (COS). Usually COS is present to the extent of only several hundred parts per million (ppm) by weight. However, even this small amount is normally beyond the allowable limits of an acceptable product. Since carbonyl sulfide is almost always formed when carbon, oxygen, and sulfur or their compounds, such as carbon monoxide, carbon disulfide and the like, are brought together at high temperatures, this compound is most frequently found in the hydrocarbon feedstocks resulting from thermal and/or catalytic cracking operations, although, in some cases, it has been found in virgin petroleum fractions.

To some extent, carbonyl sulfide is not as reactive as its companion in hydrocarbons, hydrogen sulfide. According to Kirk-Othmer's *Encyclopedia of Chemical Technology*, Vol. 13, pages 384–386, 1954 edition, carbonyl sulfide reacts slowly with the aqueous alkali-metal hydroxides and is only slowly hydrolyzed to carbon dioxide and hydrogen sulfide. This relatively unreactive characteristic of carbonyl sulfide makes it extremely difficult to remove from petroleum streams by conventional desulfurization techniques.

The presence of COS, even at very low concentrations, oftentimes renders olefins valueless for many purposes. For example, high purity olefins are required for the satisfactory production of many polymeric products, especially those useful as plastics, including polymers of ethylene, propylene, and the like. As a result, there has been a real need to improve techniques for removing COS from hydrocarbons, especially those used for polymer production.

Some of the known methods for removing carbon oxysulfide (COS) from hydrocarbon streams include the following. In British Patent Specification No. 1,142,339, published Feb. 5, 1969, the inventors teach a process for the removal of COS from gas mixtures in which unsaturated compounds such as propyne and propadiene are present, comprising passing said mixtures in liquid phase at atmospheric or superatmospheric pressures over a substance which contains one or more of the oxides of cadmium, zinc, nickel or cobalt supported on a carrier. It is stated that this process reduces the COS concentration to less than one (1) ppm.

U.S. Pat. No. 4,290,879 to Woodall et al, teaches the removal of carbonyl sulfide from propane and other similar liquified petroleum gas products by mixing liquid methanol with the untreated liquified gas and subsequently contacting the liquid mixture with solid potassium hydroxide. The COS concentration is reduced to less than one (1) ppm by volume.

U.S. Pat. No. 3,315,003 to Khelghatian, teaches that carbonyl sulfide can be effectively removed from normally gaseous hydrocarbons by first liquifying the hydrocarbons and then contacting them with soda-lime. The effluent gas must subsequently be dried to remove the moisture therefrom.

U.S. Pat. No. 3,284,531 to Shaw et al, teaches that COS can be removed by passing a fluid hydrocarbon through a bed of an anhydrous, weakly basic, anion exchange resin.

U.S. Pat. No. 3,282,831 to Hamm, discloses a method for removing COS from a hydrocarbon stream by utilizing an anionic exchange resin which is in the hydroxyl cycle and which is not fully hydrated.

The problems in purifying propylene and the like olefins are singularly complicated by the nearly identical boiling points of propylene and COS which makes COS removal by fractionation unsuitable. As a result, the levels of COS impurity in propylene stocks are often times intolerably high.

Still other disadvantages are encountered in the heretofore known procedures for the removal of COS from hydrocarbons, particularly those to be used for olefin polymerization. For example, some of the established methods introduce water or other contaminants into the hydrocarbon stream, all of which must be removed by additional processing in order to place the hydrocarbon in suitable condition for use. Any such additional processing, as well as any requirement to employ elevated temperatures adds materially and undesirably to the cost of the operation.

None of the above methods can reduce the COS content to less than fifty (50) parts per billion (ppb) by weight. Accordingly, it can be seen that there is a need for a process to reduce the COS concentration in a hydrocarbon stream to 50 ppb by weight or lower.

SUMMARY OF THE INVENTION

The present invention is directed to a process for the removal of carbonyl sulfide from hydrocarbon feedstocks, and more particularly from olefinic hydrocarbon feedstocks containing propylene. In accordance with the present invention, COS is removed by passing the hydrocarbon feed over an absorbent material comprising zinc oxide and a promoter selected from the group consisting of alumina, silico-aluminas and any combination thereof. The promoter may further comprise calcium oxide. The amount of promoter should not exceed 15% by weight of the absorbent material. The present invention reduces the carbonyl sulfide concentration in the hydrocarbon feed to 50 ppb by weight or lower.

DETAILED DESCRIPTION OF THE PREFERRED EMBODIMENTS

The present invention relates to the removal of carbonyl sulfide (COS), sometimes referred to as carbon oxysulfide, from liquid hydrocarbon streams. Of particular interest is the treatment of liquid hydrocarbon streams containing olefins which streams are to be subsequently subjected to polymerization using polymerization catalysts. As stated previously, hydrocarbon streams containing propylene present a special problem because of the nearly identical boiling points of propylene and COS. While the subsequent discussion may describe the invention in terms of treating propylene feeds, it should be understood that the present invention is applicable to the treatment of liquid hydrocarbon streams in general and olefinic liquid hydrocarbon streams in particular, i.e., hydrocarbon streams containing ethylene, propylene, butenes or any combination thereof.

The process of the present invention reduces the COS concentration in the treated hydrocarbon feedstock to not greater than 50 parts per billion by weight (ppb). The original COS concentration may be as high as 1000 parts per million by weight (ppm) or higher depending on the process of making and the origin of the hydrocarbon feedstock. Due to the expense and specialization of the present invention, it is preferred to utilize other less costly and less complex processes to reduce the COS concentration to 70 ppm or less prior to treatment with the present invention.

The absorbent material of the present invention comprises zinc oxide and a promoter selected from the group consisting of alumina, silico-aluminas and any combination thereof. The promoter may additionally comprise calcium oxide. Preferably, the absorbent material consists essentially of from about 85 to about 95 percent by weight (wt. %) of zinc oxide, from about 3 to about 10 wt. % of alumina, silico-aluminas or a combination thereof, and from about 0 to about 5 wt. % of calcium oxide.

The specific surface area of the absorbent material is preferably from about 20 to about 100 m$^2$/g and most preferably from about 30 to about 80 m$^2$/g. Obviously, absorbent materials having a higher specific surface area may be used, however, such does not result in significant advantages. On the other hand, absorbent materials having a specific surface area of less than 20 m$^2$/g do not have a sufficient absorption capacity and their catalytic activity is lower than preferred. It is also advantageous to use absorbent material in finely divided form. In general, it is preferred that the particle size does not exceed 2 mm while a particle size of from about 0.5 to about 1.5 mm is most preferred.

In utilizing the latest generation of Ziegler-type catalysts in the production of polypropylene, it is essential that the propylene feedstock contain less than 50 ppb and preferably less than 30 ppb of COS. It has been unexpectedly found that by passing the propylene feedstock over an absorbent material consisting essentially of 85 to 95 wt. % zinc oxide, 3 to 10 wt. % alumina (AL$_2$O$_3$), and 0-5 wt. % calcium oxide, the feedstock obtained has a COS content not exceeding 30 ppb. This result is unexpected due to the degree of purity obtained with a catalyst based on zinc oxide and due to the fact that this process may be carried out either in the presence or absence of water.

In polypropylene production, the liquid hydrocarbon feedstock generally comprises more than 75 wt. % propylene, more particularly, from about 85 to about 99 wt. % propylene, and from about 1 to about 10 ppm COS. In one embodiment of the present invention, the liquid propylene feedstock is passed over the absorbent material at a temperature of from about 0° C. to about 90° C. and under sufficient pressure to keep the medium in the liquid phase. The liquid hourly space velocity (LHSV) utilized is from about 0.1 to about 20 and preferably from 0.2 to about 15.

It should be noted that the quantity of promoter is critical. In fact, to obtain residual COS contents of 30 ppb or less, it is necessary to add a quantity of promoter to the zinc oxide wherein said quantity does not exceed 15 wt. % of the absorbent material.

In a preferred embodiment, at least from 3 to 10 wt. % of alumina is utilized as the promoter. However, it is preferred to utilize as the promoter from 3 to 10 wt. % alumina and from 0.5 to 5.0 wt. % calcium oxide. If the promoter represents more than 15 wt. % of the absorbent material or catalyst, the COS removal ability deteriorates resulting in liquid hydrocarbon feedstock containing unacceptable levels of COS.

The examples which follow are given in order to provide a better illustration of the process of the present invention, but without thereby restricting its scope.

EXAMPLE 1

A liquid hydrocarbon feedstock containing 99% of propylene and having a residual COS content of 2.7 ppm was passed over an absorbent material consisting essentially of 92% zinc oxide, 5% Al$_2$O$_3$ and 3% of CaO, which was finely divided to give an average particle size of about 1 mm.

The specific surface area of this material was 44 m$^2$/g.

The above mentioned feedstock was thus passed over the absorbent material at ambient temperature, at a pressure adjusted to keep the feedstock in the liquid phase, and at an LHSV of 5.

The purified feedstock had a COS content of about 25 ppb.

EXAMPLE 2

A liquid hydrocarbon feedstock containing 99% of propylene and having a residual COS content of 1.5 ppm was passed over the absorbent material used in Example 1.

The specific surface area of this material was 44 m$^2$/g.

The feedstock was thus passed over the absorbent material at a temperature of 5° C., at a pressure adjusted to keep the feedstock in the liquid phase at this temperature, and at an LHSV of 5.

The purified feedstock had a COS content of about 18 ppb.

By way of comparison, the same feedstock was passed over an absorbent material consisting essentially of 100% by weight of zinc oxide. This material had a specific surface area of 10 m$^2$/g.

The operation was carried out at a temperature of 5° C. and at a sufficient pressure to keep the feedstock in the liquid phase.

This feedstock was passed over the absorbent at an LHSV of 5.

The purified feedstock had a COS content of about 1.2 ppm.

This comparative example shows the importance of the presence of the promoter in the catalyst.

EXAMPLE 3

A liquid hydrocarbon feedstock containing 99% of propylene and having a residual COS content of 1.5 ppm was passed over an absorbent material consisting essentially of 89% ZnO, 7% Al$_2$O$_3$ and 4% CaO, which was finely divided to give an average particle size of less than 2 mm with a high proportion between 1 and 1.5 mm.

The specific surface area of this material was 30 m²/g.

The above mentioned feedstock was thus passed over the absorbent material at a temperature of 5° C., at a pressure adjusted to keep the feedstock in the liquid phase, and at an LHSV of 5.

The purified feedstock had a COS content of about 12 ppb.

The same feedstock was passed over the same absorbent material at the same temperature and pressure but at an LHSV of 17. Under these conditions, the residual COS content of the purified feedstock was 45 ppb.

By way of comparison, 45.6 g of commercial alumina were taken; this was in cylindrical shape of about 5 mm diameter and had a specific surface area of 250 m²/g. It was calcined at 500° C. and impregnated with a solution of $Zn(NO_3)_2.4H_2O$, and calcined again.

The final catalyst contained 50.4% by weight of ZnO and the final specific surface area of the material was 153 m²/g.

The same feedstock as that described above was treated on the catalyst at a temperature of 5° C., at a sufficient pressure to keep the feedstock in the liquid phase, and at an LHSV of 5.

Under these conditions, the residual COS content of the purified feedstock was 345 ppb.

What we claim is:

1. A process for removing carbonyl sulfide from a liquid olefinic hydrocarbon feedstock comprising:
   (a) passing said hydrocarbon feedstock over an absorbent material comprising zinc oxide and a promoter selected from the group consisting of alumina, silico-aluminas and any combination thereof wherein the promoter is present in amounts from about 3 to about 15 percent by weight of the absorbent material; and
   (b) recovering a liquid olefinic hydrocarbon stream having a substantially reduced carbonyl sulfide content.

2. The process of claim 1 wherein said promoter additionally comprises calcium oxide.

3. The process of claim 1 wherein said absorbent material has a particle size of smaller than 2 mm, preferably from about 0.5 to about 1.5 mm.

4. The process of claim 1 wherein said absorbent material has a specific surface area of from about 20 to about 100 m²/g, preferably from about 30 to about 80 m²/g.

5. The process of claim 1 wherein the hydrocarbon feedstock comprises at least 75% by weight of propylene.

6. The process of claim 5 wherein the absorbent material comprises from about 85 to about 95% by weight zinc oxide, from about 3 to about 10% alumina, and from about 0 to about 5% calcium oxide.

7. The process of claim 5 carried out at a temperature of from about 0° C. to about 90° C., at a sufficient pressure to retain the feedstock in liquid phase, and at a LHSV of from about 0.1 to about 20.

8. The process of claim 1 wherein the recovered hydrocarbon stream has a carbonyl sulfide concentration not exceeding 50 parts per billion by weight.

9. A process for removing carbonyl sulfide from a liquid hydrocarbon feedstock containing propylene, said process comprising the steps of:
   (a) passing said hydrocarbon feedstock over an absorbent material consisting essentially of zinc oxide and from about 3 to about 15% by weight of a promoter selected from the group consisting of alumina, silico-aluminas and any combination thereof for a time sufficient to reduce the carbonyl sulfide concentration in the feedstock to a concentration not exceeding fifty parts per billion by weight; and
   (b) recovering a liquid hydrocarbon stream having reduced carbonyl sulfide content.

10. The process of claim 9 wherein said promoter additionally comprises calcium oxide.

11. The process of claim 9 wherein said absorbent material has a particle size of smaller than 2 mm, preferably from about 0.5 to about 1.5 mm.

12. The process of claim 9 wherein said absorbent material has a specific surface area of from about 20 to about 100 m²/g, preferably from about 30 to about 80 m²/g.

13. The process of claim 9 wherein the hydrocarbon feedstock comprises at least 75% by weight of propylene.

14. The process of claim 9 wherein the absorbent material comprises from about 85 to about 95% by weight zinc oxide, from about 3 to about 10% alumina, and from about 0 to about 5% calcium oxide.

15. The process of claim 9 carried out at a temperature of from about 0° C. to about 90° C., at a sufficient pressure to retain the feedstock in liquid phase, and at a LHSV of from about 0.1 to about 20.

16. The process of claim 9 wherein the hydrocarbon feedstock comprises at least 95% by weight of propylene.

17. A process for removing carbonyl sulfide from a liquid propylene feedstock, comprising:
   (a) passing the propylene feedstock over an absorbent material comprising from about 85% to about 95% by weight zinc oxide, from about 3% to about 10% by weight of a member selected from the group consisting of alumina, silico-aluminas, and any combination thereof, and from about 0% to about 5% by weight of calcium oxide, at a temperature of from about 0° C. to about 90° C. and under sufficient pressure to retain the propylene feedstock in a liquid phase and at a liquid hourly space velocity sufficient to reduce the carbonyl sulfide concentration to a level not exceeding fifty parts per billion by weight; and
   (b) recovering treated propylene feedstock.

18. The process of claim 17 wherein the carbonyl sulfide original concentration in the propylene feed is from about 1 to about 70 parts per million by weight.

19. The process of claim 17 wherein the absorbent material has a particle size of smaller than 2 mm, preferably from about 0.5 to about 1.5 mm and a specific surface area of from about 20 to about 100 m²/g, preferably from about 30 to about 80 m²/g.

20. The process of claim 17, wherein the liquid hourly space velocity is from about 0.1 to about 20.

* * * * *